United States Patent
Jow et al.

(10) Patent No.: US 12,009,580 B2
(45) Date of Patent: *Jun. 11, 2024

(54) ANTENNA CONFIGURATION FOR COMPACT GLUCOSE MONITOR

(71) Applicant: Verily Life Sciences LLC, South San Francisco, CA (US)

(72) Inventors: Uei-ming Jow, San Jose, CA (US); Maryam Fathi, Palo Alto, CA (US)

(73) Assignees: VERILY LIFE SCIENCES LLC, South San Francisco, CA (US); DEXCOM, INC., San Diego, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/169,773

(22) Filed: Feb. 15, 2023

(65) Prior Publication Data
US 2023/0411834 A1    Dec. 21, 2023

Related U.S. Application Data

(63) Continuation of application No. 17/248,466, filed on Jan. 26, 2021, now Pat. No. 11,605,882, which is a
(Continued)

(51) Int. Cl.
*H01Q 1/22* (2006.01)
*A61B 5/07* (2006.01)
(Continued)

(52) U.S. Cl.
CPC ............ *H01Q 1/273* (2013.01); *A61B 5/076* (2013.01); *A61B 5/14532* (2013.01);
(Continued)

(58) Field of Classification Search
CPC .... H01Q 1/273; H01Q 1/2208; H01Q 1/2216; H01Q 1/38; H01Q 7/00; A61B 5/076;
(Continued)

(56) References Cited

U.S. PATENT DOCUMENTS

| 8,386,008 B2 | 2/2013 | Yuen et al. |
| 8,427,817 B2 | 4/2013 | Lewis et al. |

(Continued)

FOREIGN PATENT DOCUMENTS

| CN | 104466363 A | 3/2015 |
| CN | 104887245 A | 9/2015 |

(Continued)

OTHER PUBLICATIONS

U.S. Appl. No. 15/231,906, "Advisory Action", dated Feb. 6, 2020, 7 pages.
(Continued)

*Primary Examiner* — Hai V Tran
*Assistant Examiner* — Michael M Bouizza
(74) *Attorney, Agent, or Firm* — Kilpatrick Townsend & Stockton LLP

(57) ABSTRACT

A wearable glucose monitor may include a compact having an antenna positioned on a housing of the glucose monitor to allow the size of the antenna to be larger than a printed circuit board of the glucose monitor positioned internal to the housing. The antenna may be communicatively coupled to a wireless communication device, such as a transceiver on the PCB, to transmit glucose level measurements to an external device through low-frequency radio signals. In some aspects, the antenna may be configured to be distributed into multiple sections positioned on different sections of the housing and connected to form a complete antenna.

20 Claims, 8 Drawing Sheets

Related U.S. Application Data continuation of application No. 15/231,906, filed on Aug. 9, 2016, now Pat. No. 10,938,094.

(51) Int. Cl.
| | |
|---|---|
| *A61B 5/145* | (2006.01) |
| *H01Q 1/27* | (2006.01) |
| *H01Q 1/38* | (2006.01) |
| *H01Q 7/00* | (2006.01) |
| *H04B 5/72* | (2024.01) |
| *A61B 5/00* | (2006.01) |

(52) U.S. Cl.
CPC ......... *H01Q 1/2208* (2013.01); *H01Q 1/2216* (2013.01); *H01Q 1/38* (2013.01); *H01Q 7/00* (2013.01); *H04B 5/72* (2024.01); *A61B 5/14503* (2013.01); *A61B 5/686* (2013.01)

(58) Field of Classification Search
CPC . A61B 5/14532; A61B 5/14503; A61B 5/686; H04B 5/0031; H04B 5/72
See application file for complete search history.

(56) References Cited

U.S. PATENT DOCUMENTS

| | | |
|---|---|---|
| 8,954,135 B2 | 2/2015 | Yuen et al. |
| 9,184,490 B2 | 11/2015 | Crouther et al. |
| 10,938,094 B2 | 3/2021 | Jow et al. |
| 11,605,882 B2 | 3/2023 | Jow et al. |
| 2005/0245795 A1 | 11/2005 | Goode, Jr. et al. |
| 2009/0076360 A1 | 3/2009 | Brister et al. |
| 2009/0085768 A1 | 4/2009 | Patel et al. |
| 2009/0322630 A1 | 12/2009 | Friman et al. |
| 2011/0213225 A1 | 9/2011 | Bernstein et al. |
| 2011/0288388 A1 | 11/2011 | Shah et al. |
| 2012/0245444 A1 | 9/2012 | Otis et al. |
| 2014/0163338 A1 | 6/2014 | Roesicke |
| 2014/0266939 A1 | 9/2014 | Baringer et al. |
| 2014/0275898 A1 | 9/2014 | Taub et al. |
| 2015/0116168 A1 | 4/2015 | Yosui |
| 2015/0289814 A1 | 10/2015 | Magar et al. |
| 2015/0364938 A1 | 12/2015 | Lapetina et al. |
| 2017/0045916 A1* | 2/2017 | Kim ........................ H01Q 1/48 |
| 2017/0047636 A1 | 2/2017 | Lee et al. |
| 2018/0048056 A1 | 2/2018 | Jow et al. |
| 2018/0062275 A1* | 3/2018 | Kim ..................... H01Q 1/2208 |
| 2020/0068054 A1 | 2/2020 | Kim et al. |

FOREIGN PATENT DOCUMENTS

| | | |
|---|---|---|
| TW | 201813196 A | 4/2018 |
| WO | 2018031161 A1 | 2/2018 |

OTHER PUBLICATIONS

U.S. Appl. No. 15/231,906 , "Final Office Action", dated Oct. 21, 2019, 8 pages.
U.S. Appl. No. 15/231,906 , "Non-Final Office Action", dated Apr. 2, 2020, 11 pages.
U.S. Appl. No. 15/231,906 , "Non-Final Office Action", dated Apr. 5, 2019, 9 pages.
U.S. Appl. No. 15/231,906 , "Notice of Allowance", dated Oct. 13, 2020, 9 pages.
U.S. Appl. No. 15/231,906 , "Restriction Requirement", dated Oct. 4, 2018, 9 pages.
U.S. Appl. No. 17/248,466 , "Non-Final Office Action", dated Oct. 5, 2022, 14 pages.
U.S. Appl. No. 17/248,466 , "Notice of Allowance", dated Nov. 4, 2022, 9 pages.
International Application No. PCT/US2017/041423 , "International Preliminary Report on Patentability", dated Feb. 21, 2019, 12 pages.
International Application No. PCT/US2017/041423 , "International Search Report and Written Opinion", dated Oct. 16, 2017, 6 pages.
Taiwanese Application No. 106125195 , "Notice of Decision to Grant", dated Mar. 23, 2021, 3 pages.
Taiwanese Application No. 106125195 , "Office Action", dated Dec. 16, 2020, 8 pages.

* cited by examiner

ANTENNA CONFIGURATION FOR COMPACT GLUCOSE MONITOR

CROSS-REFERENCE TO RELATED APPLICATIONS

This application is a continuation of U.S. patent application Ser. No. 17/248,466, filed Jan. 26, 2021, which is a continuation of U.S. patent application Ser. No. 15/231,906, filed Aug. 9, 2016, the entirety of both of which are hereby incorporated by reference.

TECHNICAL FIELD

The present disclosure generally relates to antenna systems, and, more particularly, although not necessarily exclusively, to configurations for antennas in compact glucose monitoring systems.

BACKGROUND

As electronic devices decrease in size, the area on a printed circuit board to configure electronic components of the electronic device becomes increasingly limited. The limited area may affect the size of antennas mounted on the printed circuit board and certain antennas, such as low-frequency antennas, may require a large coupling area to efficiently transmit and receive radio frequency signals. Thus, decreasing the size of the printed circuit board on which the antenna is mounted may limit the available space on the printed circuit board to position the antenna and compromise the operability of the antenna.

SUMMARY

In some aspects of the present disclosure, a wearable glucose monitor may include an antenna positioned on the glucose monitor's housing to transmit glucose measurements from a glucose sensor to an external computing device proximate to the glucose monitor. The glucose monitor antenna and the sensor may be communicatively coupled to a printed circuit board ("PCB") disposed in the housing and supporting the glucose monitor's electrical components. Positioning the antenna on the housing rather than the PCB may allow the antenna to have a larger coupling area to the glucose monitor without enlarging the glucose monitor to accommodate a larger PCB for the antenna.

In one aspect, a wearable device includes a device housing. The wearable device also includes a PCB disposed in the device housing and communicatively coupled to a glucose sensor. The PCB includes a wireless communication device mounted on the PCB. The wearable device also includes an antenna communicatively coupled to the wireless communication device. The antenna includes a coil that is disposed on the device housing. An area enclosed by a perimeter of the coil disposed on the device housing is larger than an area of the PCB.

In another aspect, a method includes providing a PCB, a glucose sensor, a wireless communication device, an antenna, and a housing of a glucose monitor. The method also includes coupling the glucose sensor and the wireless communication device to the PCB. The method also includes positioning the antenna on a surface of the housing. A coupling area defined by an outer trace of the antenna on the housing is larger than an area of the PCB. The method also includes enclosing the PCB within the housing.

In another aspect, a method includes receiving, by a glucose sensor communicatively coupled to PCB of a wearable glucose monitor, a first glucose level measurement. The method also includes transmitting, by a processor on the PCB, an electrical signal representing the first glucose level measurement to a wireless communication device on the printed circuit board. The wireless communication device is communicatively coupled to an antenna comprising a coil disposed on a housing of the wearable glucose monitor. A coupling area defined by an outer trace of the coil disposed on the housing is larger than an area of the PCB. The method also includes transmitting, by the antenna, a radio frequency signal representing the first glucose level measurement to an external device having a database for storing a plurality of glucose level measurements received from the wearable glucose monitor. The plurality of glucose level measurements include the first glucose level measurement.

These illustrative examples are mentioned not to limit or define the scope of this disclosure, but rather to provide examples to aid understanding thereof. Illustrative examples are discussed in the Detailed Description, which provides further description. Advantages offered by various examples may be further understood by examining this specification.

BRIEF DESCRIPTION OF THE DRAWINGS

The accompanying drawings, which are incorporated into and constitute a part of this specification, illustrate one or more certain examples and, together with the description of the example, serve to explain the principles and implementations of the certain examples.

DETAILED DESCRIPTION

Figure 1:
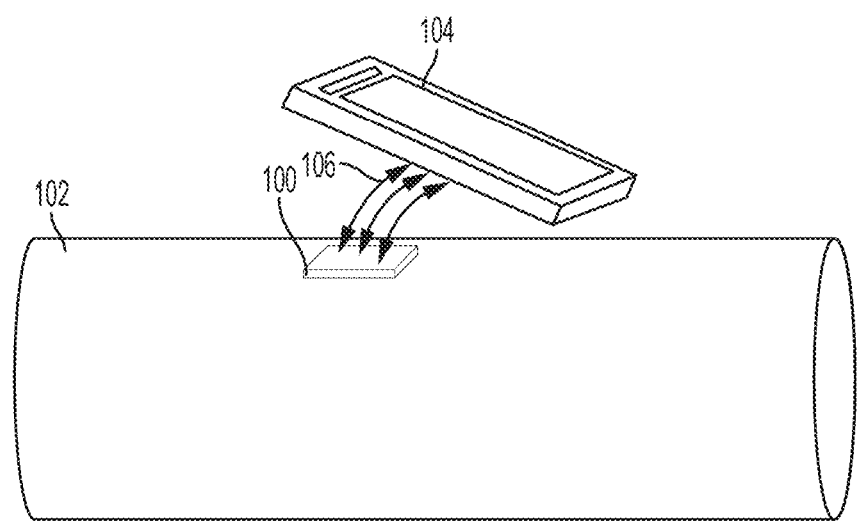
FIG. 1 is a perspective view of a glucose monitor that may include an antenna configuration according to aspects of the present disclosure.

Certain aspects and examples of the present disclosure relate to antenna configurations for a continuous glucose monitor. In one illustrative example, a continuous glucose monitor has a compact housing, approximately three centimeters in diameter, that encloses a small printed circuit board ("PCB"). The PCB includes sensing circuitry that is connected to a glucose sensor that penetrates a patient's skin and senses glucose concentration in the patient's interstitial fluid. The sensing circuitry is also connected to an antenna that is formed on the outside of the housing, which allows the glucose monitor to transmit sensor information to a computing device, such as a tablet, computer, or smartphone. In this example, the antenna has a coil shape and is sized to extend to the edges of the housing to provide as large an antenna is possible. In this example, by forming the antenna on the housing, rather than on the PCB, the PCB can be made smaller, while the sensor retains a larger antenna, which can improve wireless performance.

Examples according to this disclosure can provide a compact glucose monitor for extended wear by a patient, without compromising the size and operability of the glucose monitor's antenna. In some aspects, the antenna may be communicatively coupled to circuitry on a printed circuit board ("PCB") of the glucose monitor, but may be physically separate from the PCB. For example, the antenna may be positioned on the glucose monitor's housing to provide an enlarged surface area for the antenna. In other aspects, the housing of the glucose monitor may include a metal material that may be configured to allow the housing itself to operate as the glucose monitor's antenna. In additional aspects, the antenna may be distributed between multiple antenna portions that, when combined, form a complete antenna for the glucose monitor. In some examples, the housing of the antenna may include separate connectable portions that envelope the PCB of the glucose monitor when the connectable portions are connected. The antenna may be distributed to allow each antenna section to be positioned on a different portion of the housing.

Antenna configurations according to some aspects of the present disclosure may provide additional space for an antenna to be positioned than a PCB of a compact glucose monitor. In some aspects, the performance of the antenna is related to the size of the antenna. A larger antenna can provide a larger "coupling area" to provide better wireless communications with another device. In some aspects, the antenna may have a perimeter defining a coupling area that is larger than the area of the PCB. Physically separating the antenna from the PCB may allow the size of the overall glucose monitor to be reduced without compromising the coupling area of the antenna needed to operate efficiently. Further, the positioning of the antenna of the antenna may allow the antenna to be closer to an antenna of an external reader or transceiver. The closer proximity between the glucose monitor antenna and the external antenna may result in noticeable improvement of the communication. Also, antennas mounted to a PCB may be limited not only by the available area on the PCB, but may also be limited to planar configurations because PCBs tend to be flat.

Detailed descriptions of certain examples are discussed below. These illustrative examples are given to introduce the reader to the general subject matter discussed here and are not intended to limit the scope of the disclosed concepts. The following sections describe various additional aspects and examples with reference to the drawings in which like numerals indicate like elements, and directional descriptions are used to describe the illustrative examples but, like the illustrative examples, should not be used to limit the present disclosure. The various figures described below depict examples of implementations for the present disclosure, but should not be used to limit the present disclosure.

Various aspects of the present disclosure may be implemented for wireless communication in various scenarios. FIG. 1 is a perspective view of a glucose monitor 100 that may include an antenna configuration according to aspects of the present disclosure. In some aspects, the glucose monitor 100 may be a biomedical device for measuring biological parameters of a patient, such as a diabetic patient's glucose levels. The glucose monitor 100 may be a wearable device attached to a patient's skin 102 by an adhesive layer on a glucose monitor's 100 housing surface a band (not shown), or by other attaching means. In some aspects, the glucose monitor 100 may include one or more invasive or non-invasive sensor devices for measuring a patient's biological parameters and may use a transceiver coupled to an antenna positioned on the glucose monitor's 100 housing to communicate the parameter measurements to an external device 104. The antenna may be positioned on an external or internal surface of the housing to allow a larger surface area for the antenna. Positioning the antenna on the housing instead of the PCB disposed in the housing may allow for a larger antenna without enlarging the size of the glucose monitor to accommodate a larger PCB for a larger antenna. The antenna's positioning may also allow for a smaller glucose monitor as PCB's size may be reduced without disturbing the size of the antenna.

The glucose monitor 100 may be compact in size for placement on a patient's skin 102. In some aspects, because the glucose monitor is compact in size, the glucose monitor 100 may remain on the skin 102 for an extended period of time with minimal discomfort to the patient. For example, the glucose monitor 100 may be positioned on a patient's arm and remain in place on the arm for several days to provide glucose level measurements at regular intervals (e.g., every minute, every hour, etc.). The glucose monitor's 100 compact nature may also allow the glucose monitor 100 to be worn on a larger variety of areas on the patient's skin. For example, the glucose monitor 100 may be sized for placement on a larger body part, such as an arm or leg, or may be sufficiently compact for placement on a smaller body part, such as a patient's hand or finger.

The external device 104 may include a computing device having one or more communication devices that can wirelessly communicate with the glucose monitor 100. In some aspects, the external device 104 may be a handheld computing device, such as a smartphone, personal digital assistant, or tablet. In other aspects, the external device 104 may represent any computing device including, but not limited to, a desktop computer, a laptop, or a wearable device (e.g., a smartwatch), having wireless communication means for wireless communication with the glucose monitor 100. In additional and alternative aspects, the external device 104 may include a processor for analyzing measurements received from the glucose monitor 100 or a database for storing such measurement.

In FIG. 1, the external device 104 is shown in close proximity to the glucose monitor 100. Arrows 106 represent a wireless coupling of the glucose monitor 100 and the external device 104 for wireless communication between the devices. In some aspects, the coupling range for the coupling of the glucose monitor 100 and the external device 104 may be include a range between 0 and 25 centimeters.

Figure 2:
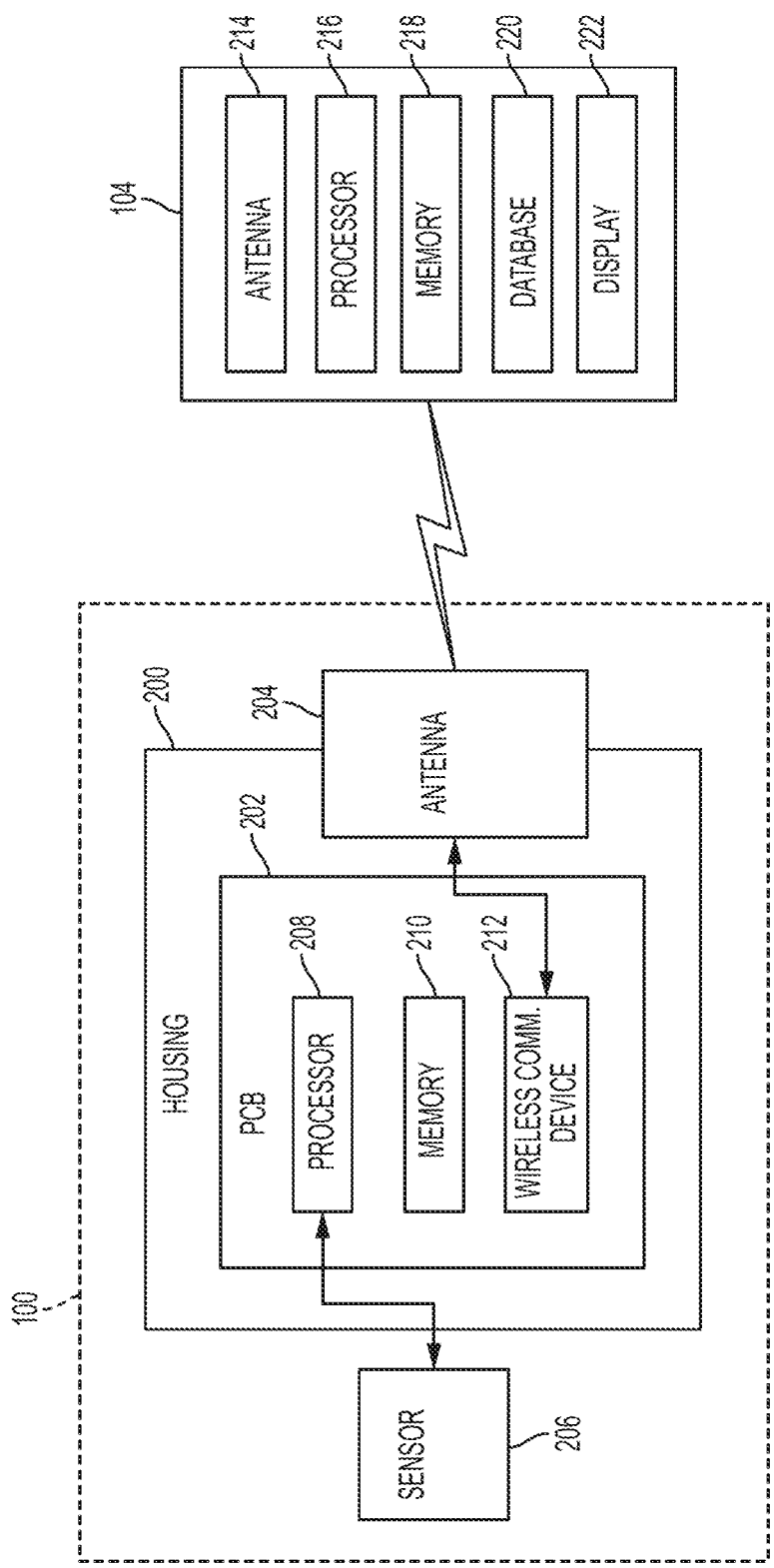
FIG. 2 is a block diagram of the glucose monitor of FIG. 1 according to aspects of the present disclosure.

FIG. 2 is a block diagram of the glucose monitor 100 according to aspects of the present disclosure. The glucose monitor 100 includes a housing 200. In some aspects, the housing 200 may house all of the components of the glucose monitor 100. For example, the housing 200 may include a printed circuit board ("PCB") positioned internal to the housing 200, an antenna 204 positioned on a surface of the housing, and include a sensor 206 extending from the housing 200. The housing 200 may have any suitable shape. In some aspects, the housing 200 may include at least one side or section having a linear or planar surface for positioning the housing 200 on the skin 102 of a patient as described in FIG. 1. In additional and alternative aspects, the housing 200 may include sides having a circular or polygonal shape, such as a rectangular shape. The housing 200 may be made of any suitable material for housing the PCB 202. Non-limiting examples of materials that may be suitable for the housing 200 include polyethylene, polyvinyl chloride ("PVC"), polypropylene, nylon, polyurethane, polycarbonate, steel, aluminum, and other plastics and metals.

The housing 200 may be compact in size to allow placement of the housing on the skin 102 of a patient for extended wear. In some aspects, the housing 200 of the glucose monitor 100 may have a circular or other rounded cross-sectional shape having a diameter (or diameter-like measurement for non-circular, rounded shapes such as an oval shape) measuring less than approximately 2 inches (or approximately 5 centimeters). Similarly, in another example, the housing 200 may have a polygonal shape with a width or length measuring less than approximately 2 inches (or approximately 5 centimeters).

The PCB 202 positioned inside the housing 200 may include conductive traces, or other features etched into a surface of the PCB 202 to incorporate the electrical components of the glucose monitor 100. In some aspects, the PCB 202 may be a single-sided, double-sided, or multi-layered PCB The antenna 204 may be positioned on a surface of the housing 200. In some aspects, the antenna 204 may include a coil. The coil may be positioned or otherwise disposed on either the housing's 200 internal or external surface. In at least one example, the coil may include conjoined, concentric figures positioned around a common axis. In some aspects, the housing 200 may include multiple sections and the antenna 204 may be distributed into multiple antenna sections positioned on a corresponding housing section. The multiple antenna sections of the distributed antenna section may be connected to form a complete antenna for transmitting or receiving radio frequency signals. In some aspects, the antenna 204 may include a low-frequency antenna. In some aspects, the antenna 204 may be tuned for transmitting and receiving radio frequency signals in the range of 100 kHz to 100 MHz. Non-limiting examples of the antenna 204 operating in a lower frequency range may include a near-field communication ("NFC") antenna, a radio-frequency identification ("RFID") antenna, or other means for wirelessly communicating in a lower frequency range. In one example, the antenna 204 may include an NFC antenna tuned for a frequency of 13.56 MHz. In another example, the antenna 204 may include an RFID antenna tuned for a frequency range of 120-150 kHz. In other examples, the RFID antenna may be tuned for larger frequencies, such as 13.56 MHz.

In additional and alternative aspects, the antenna 204 may include a high-frequency antenna. For example, the antenna 204 may be tuned for transmitting and receiving radio frequency signals in the range of 1 GHz to 5 GHZ. Non-limiting examples of the antenna 204 operating in the higher frequency range may include a Bluetooth, wireless local area network ("WLAN") antenna, or other means for wirelessly communicating in a higher frequency range. In additional aspects, the glucose monitor 100 may include multiple antennas positioned on the housing 200. For example, the glucose monitor 100 may include both a high-frequency antenna and a low-frequency antenna positioned on the housing 200.

The size of the antenna 204 may affect the frequency range at which the antenna 204 may be tuned. In some aspects, the antenna 204 may have a large coupling area corresponding to an area of the surface of the housing 200 on which the antenna 204 is formed or attached defined by an outer trace of the antenna 204. For example, in some aspects, placing the antenna 204 on the housing may allow the coupling area of the antenna 204 to include a region that is larger than the area of the PCB 202. The size of the antenna 204 and the frequency range of the antenna 204 may also affect the wireless coupling range to the external device 104. For instance, a larger antenna 204 may have a longer range.

Though the antenna 204 may be positioned on the housing 200 and physically separate from the PCB 202, the antenna 204 may be communicatively coupled to one or more components on the PCB 202. For example, the antenna 204 may be connected to a component on the PCB 202 by a lead, which may extend through a surface of the housing 200 in aspects where the antenna 204 is positioned on an external surface of the housing 200. In some aspects, the antenna 204 may have a planar shape, such as a spiral trace on the housing. In other aspects, the shape of the antenna 204 may conform to the shape of housing surface on which it is positioned.

The sensor 206 of the glucose monitor 100 may include one or more invasive or non-invasive glucose sensors for measuring a patient's glucose levels. In some aspects, the sensor 206 may include a non-invasive glucose sensor positioned on or proximate to a surface of the skin 102 of the patient to record glucose level measurements. For example, the non-invasive glucose sensor may include a laser or other means for measuring glucose levels without piercing the skin 102. In other aspects, the sensor 206 may include an invasive glucose sensor that may be inserted into the subcutaneous tissue of the skin to extract or interact with electrolytes from the patient to measure glucose levels. For example, the glucose sensor may include one or more electrodes insertable into a patient's skin to expose the electrodes to interstitial fluid. The electrodes may include a glucose oxidase ("GOX") coating to react with glucose present in the interstitial fluid and creates reaction products, such as hydrogen peroxide. A voltage may be applied to the electrodes and an electrical current may be generated based on the amount of the reaction products. The strength of the current may be used to determine the patient's glucose levels.

The sensor 206 may be coupled to the PCB 202 through a processor 208 positioned on the PCB. In some aspects, the sensor 206 may be coupled to the processor 208 through a conductive wire or other material, such as a spring, extending from the sensor 206 to the processor 208. The processor 208 may receive glucose level measurements from the sensor 206.

A wireless communication device 212, such as a transmitter, receiver, or transceiver, may also be mounted to the PCB 202. The wireless communication device 212 may be coupled to the antenna 204 to generate and receive radio signals corresponding to the information (e.g., glucose level measurements) received by the wireless communication device 112.

The antenna 204 of the glucose monitor 100 may be communicatively coupled to an antenna 214 of the external device 104. The antenna 214 may be of a type compatible to the antenna 204 to allow for communication between the glucose monitor 100 and the external device 104. For example, the antenna 214 may be tuned for NFC or RFID communications corresponding to the antenna 204. The external device 104 may also include a processor 216 and a memory 218 including instructions executable by the processor 216.

In some aspects, the memory 218 may include instructions for causing the processor 216 to store glucose level measurements of a patient received from the glucose monitor 100 in a database 220. The database 220 may include a storage device having space for storing multiple glucose level measurements. In some aspects, the database 220 may be configured to store glucose level measurements for a single patient. In other aspects, the database 220 may store glucose level measurements for multiple patients. The memory 218 may include instructions for causing the processor 216 to analyze glucose level measurements of a patient received from the glucose monitor 100. For example, the processor 216 may generate one or more user interfaces including graphs, trends, reports, or other analysis of the glucose level measurements received from the glucose monitor 100. The external device 104 also includes a display unit 222 on which the user interfaces generated by the processor 216 may be displayed. In some aspects, the display unit 22 may include a cathode ray tube, a liquid crystal display, light-emitting diodes, organic light-emitting diodes, or other displaying device for displaying the user interfaces.

Figure 3:
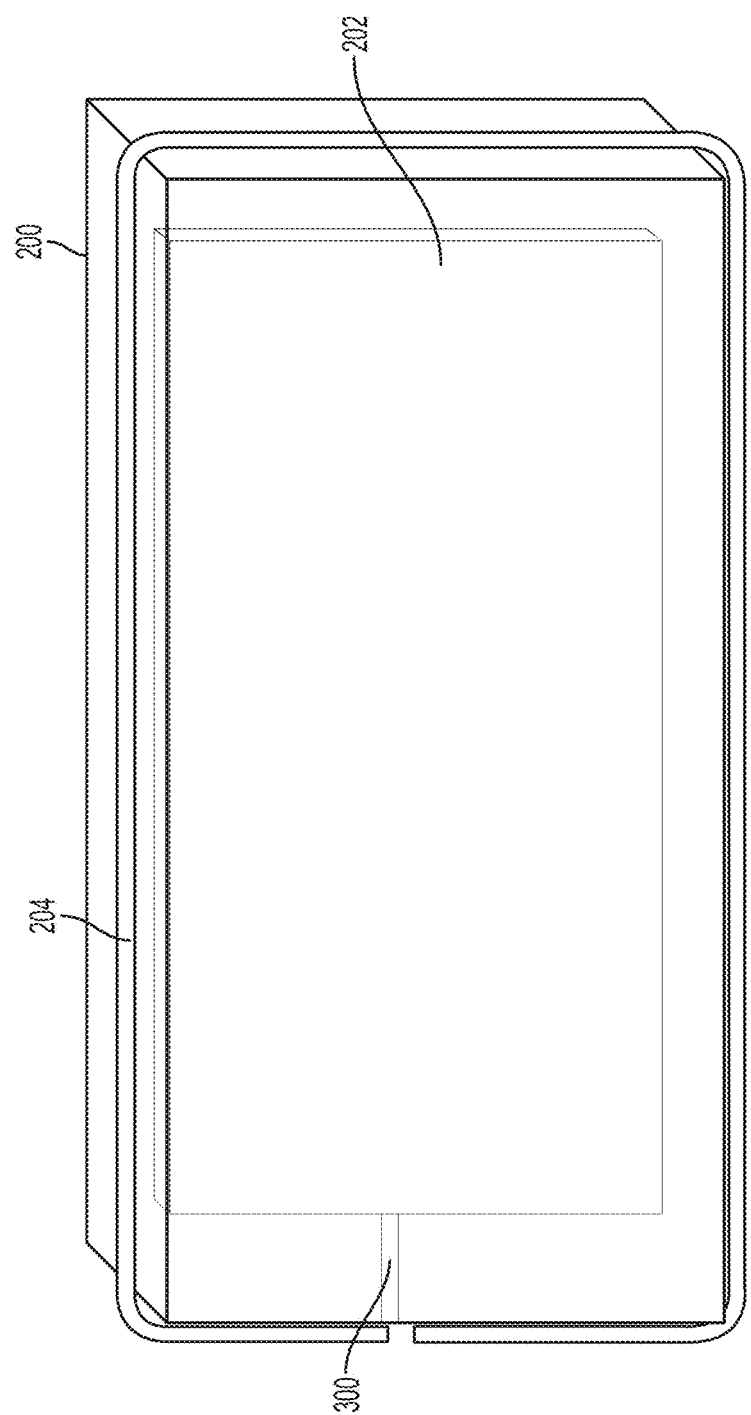
FIG. 3 is a perspective view of an example of an antenna configuration according to aspects of the present disclosure.

FIG. 3 is a partial perspective view of an example of an antenna configuration according to aspects of the present disclosure. The antenna configuration includes the antenna 204 of FIG. 2 positioned on the housing 200 of the glucose monitor 100. The PCB is positioned internal to the housing 200. Although the housing 200 is shown as having a rectangular cross-sectional shape, the housing 200 may have any shape without departing from the scope of the present disclosure. The antenna 204 may be positioned on an external or internal surface of the housing 200. In some examples, the antenna 204 may extend across multiple housing surfaces. For example, in FIG. 3, the antenna 204 is shown as extending across four housing surfaces. In some aspects, the antenna 204 may include a trace that extends across or around the entire housing surface.

A lead 300 is positioned between the PCB 202 and the antenna 204 positioned on the housing 200. The lead 300 may include a conductive wire, spring, or other structure configured to communicatively couple the antenna 204 to a component on the PCB 202. For example, the lead 300 may couple the antenna 204 to the wireless communication device 112 of FIG. 2. The signals transmitted and received by the antenna 204 may be communicated between the antenna 204 and the wireless communication device 112 through the lead 300.

Figure 4A:
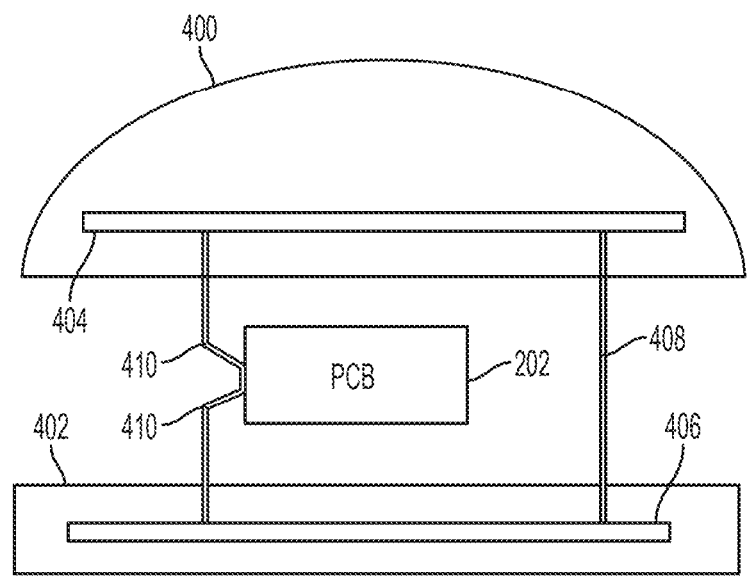
FIG. 4A is an exploded cross-sectional view of an example of a distributed antenna configuration according to aspects of the present disclosure.
Figure 4B:
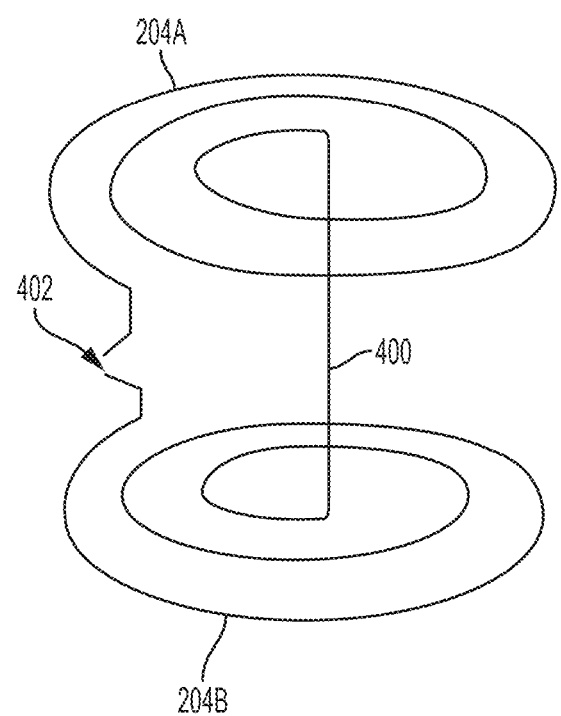
FIG. 4B is a perspective view of the distributed antenna configuration of FIG. 4A according to aspects of the present disclosure.

FIGS. 4A and 4B illustrate a distributed antenna configuration that may be included in glucose monitors according to the present disclosure. FIG. 4A is an exploded cross-sectional view of an example of a distributed antenna configuration according to aspects of the present disclosure. FIG. 4B is a perspective view of the distributed antenna configuration of FIG. 4A without the housing sections.

The housing including a top section 400 and a bottom section 402. The top section 400 has a domed shape with a semi-circular cross-section. The bottom section 402 includes a rectangular cross-section. The bottom section 402 includes a planar surface for positioning the bottom section 402 on the skin 102 of a patient. In some aspects, the bottom section 402 may include a surface having an adhesive film for placing the housing 200 onto the skin 102. In additional aspects, the sensor 206 of the glucose monitor 100 may extrude from a surface of the bottom section 402 and may be injected into the skin 102. In some aspects, a width of the bottom section 402 may be less than a width of the top section 400 to allow the top section 400 to slide over a lateral surface of the bottom section 402 to enclose the PCB 202. In other aspects, the sections 400, 402 may include corresponding features, such as ridges and gaps or other interlocking devices to connect enclose the PCB 202.

The distributed antenna includes antenna section 404 and antenna section 406. Antenna section 404 is positioned on a surface of the top section 400 of the housing and antenna section 406 is positioned on a surface of the bottom section 402 of the housing. In some aspects, the antenna sections 404, 406 may be positioned on an external surface of the housing sections 400, 402. In other aspects, the antenna sections 404, 406 may be positioned on an internal surface of the housing sections 400, 402. In additional aspects, one of the antenna sections 404, 406 may be positioned external to the housing sections 400, 402 and the other may be positioned internal to the housing sections 400, 402. In some aspects, the antenna sections 404, 406 may represent traces of the antenna positioned on an internal or external surface of the housing sections 400, 402. In other aspects, one or both of the antenna sections 404, 406 may be three-dimensional and extend radially from its respective housing section 400, 402. In some aspects, the antenna sections 404, 406 may have a spiral or coiled shape as shown in FIG. 4B. Although the housing sections 400, 402 and the antenna sections 404, 406 are shown in FIGS. 4A and 4B as having a particular shape, the housing sections 400, 402 and the antenna sections 404, 406 may have any shape without departing from the scope of the present disclosure. Also, though FIGS. 4A and 4B show two housing sections 400, 402 and two antenna sections 404, 406, the housing 200 may include any number of sections and the antenna 204 may be distributed into any number of sections without departing from the scope.

The antenna sections 404, 406 include a connection device 408 to couple the antenna sections 404, 406 and form a complete antenna 204. In some aspects, the connection device 408 may be a conductive wire, spring, or other device that communicatively couples the antenna sections 404, 406. In some aspects, the connection device 408 may extend along an external or internal surface of the housing sections 400, 402, depending on whether the antenna sections 404, 406 are positioned on an internal or external surface of the housing sections 400, 402. In other aspects, the connection device 408 may extend through the surfaces of the housing sections 400, 402 to connect to each of the antenna sections 404, 406. A feed line 410 also extends from each of the antenna sections 404, 406 to connect the antenna sections 404, 406 to the PCB 202. The feed line 410 may include a wire, spring, or other material that may extend through a housing section 400, 402 when one or both of the antenna sections 404, 406 is positioned on an external surface of the housing section 400, 402. In some aspects, the feed line may include a transmission line to communicatively couple the PCB 202 and the antenna sections 404, 406.

Figure 5:
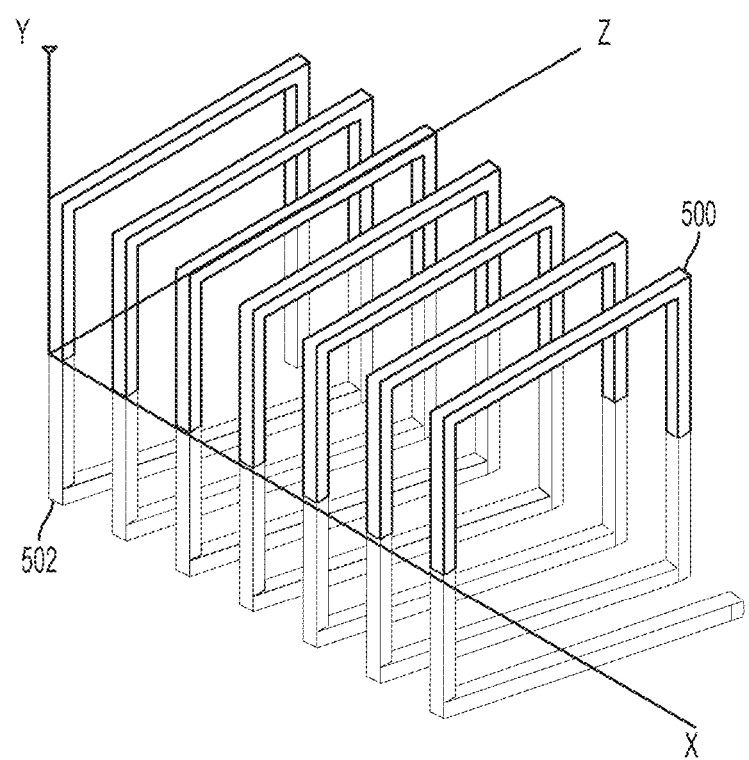
FIG. 5 is a perspective view of an example of an example distributed antenna configuration according to aspects of the present disclosure.

FIG. 5 is a perspective view of an example of an alternative distributed antenna configuration according to aspects of the present disclosure. The antenna sections 500, 502 may be communicatively coupled via a connection line (not shown) to form the antenna 204 described in FIG. 2. The antenna sections 500, 502 may each include subsections of the respective antenna section 500, 502. In some aspects, the antenna section 500 may represent the antenna section 404 of FIGS. 4A and 4B that is positioned on housing section 408 while antenna section 502 may represent the antenna section 406 that is positioned on the housing section 410.

In some aspects, the antenna sections 500, 502 may include separate traces of the antenna on an internal or external surface of the housing section. In other aspects, the antenna section may represent three-dimensional sections of a coil that are attached to the internal or external surface of the housing sections 408, 410 of FIG. 4A. The antenna sections 500, 502 may form a complete coil, such as the coil shown in FIG. 5, when the housing sections are joined together to enclose the PCB. For example, the housing may be positioned externally to the coil formed by antenna sections 500, 502, or internal to the x-axis of the antenna sections 500, 502. The antenna sections 500, 502 may be communicatively coupled by one or more connection wires between the antenna portions forming the antenna sections or by other means, such as lead points positioned on an edge portion of the housing corresponding to each endpoint of one or more of the antenna portions.

Figure 6:
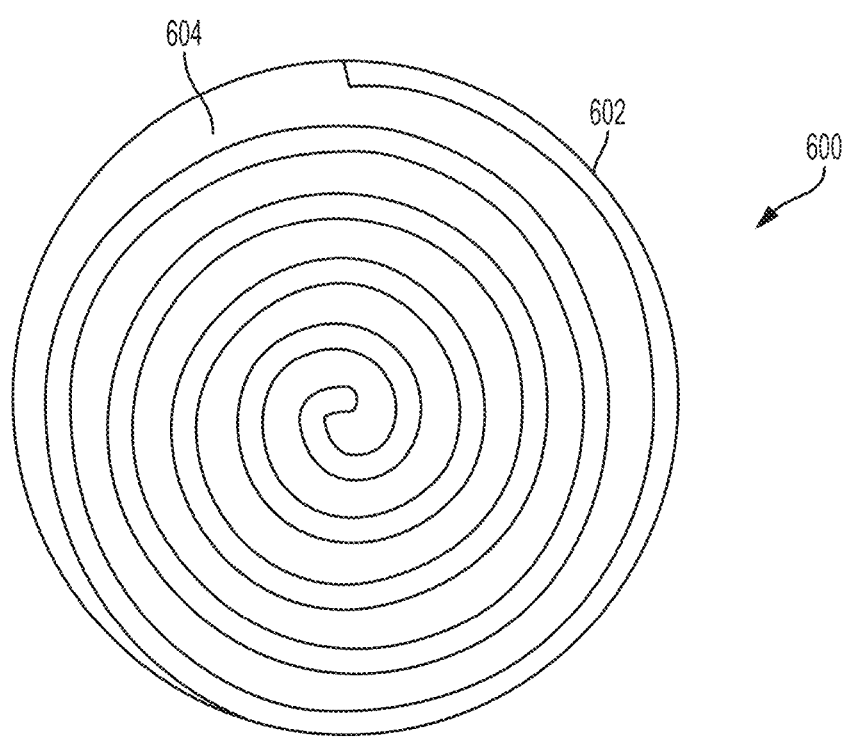
FIG. 6 is a top view of an example antenna configuration according to some aspects of the present disclosure.

FIG. 6 is a top-down view of an alternative antenna configuration according to some aspects of the present disclosure. The housing 600 may represent a housing for the glucose monitor 100 of FIG. 1. The housing 600 includes a metal material 602 forming the housing 600. The metal material 602 may include any material suitable for an antenna, including, but not limited to silver, coper, aluminum, annealed copper, or nickel.

The metal material 602 may be a contiguous surface of the housing 600. For example, FIG. 6 shows the metal material 602 in the shape of a spiral that extends from an edge of the housing 600 and winds toward the center of the housing 600. The pattern of the metal material 602 may define a non-metal region 604 of the housing 600. In some aspects, the non-metal region 604 may include etchings in the metal material 602 where the metal material 602 was removed from the housing 600. In other aspects, the metal material may include a non-conductive surface such as a plastic polymer. In some aspects, the pattern of the metal material 602 defining the non-metal region 604 may form the antenna 204 of the glucose monitor 100. The metal material 602 may be connected to the PCB 202 by a feed line or other conductor as described in FIG. 2. In some aspects, where the housing 600 represents one section of the housing 200 having multiple sections, the metal material 602 may also be connected to other antenna sections forming the antenna 204.

Figure 7:
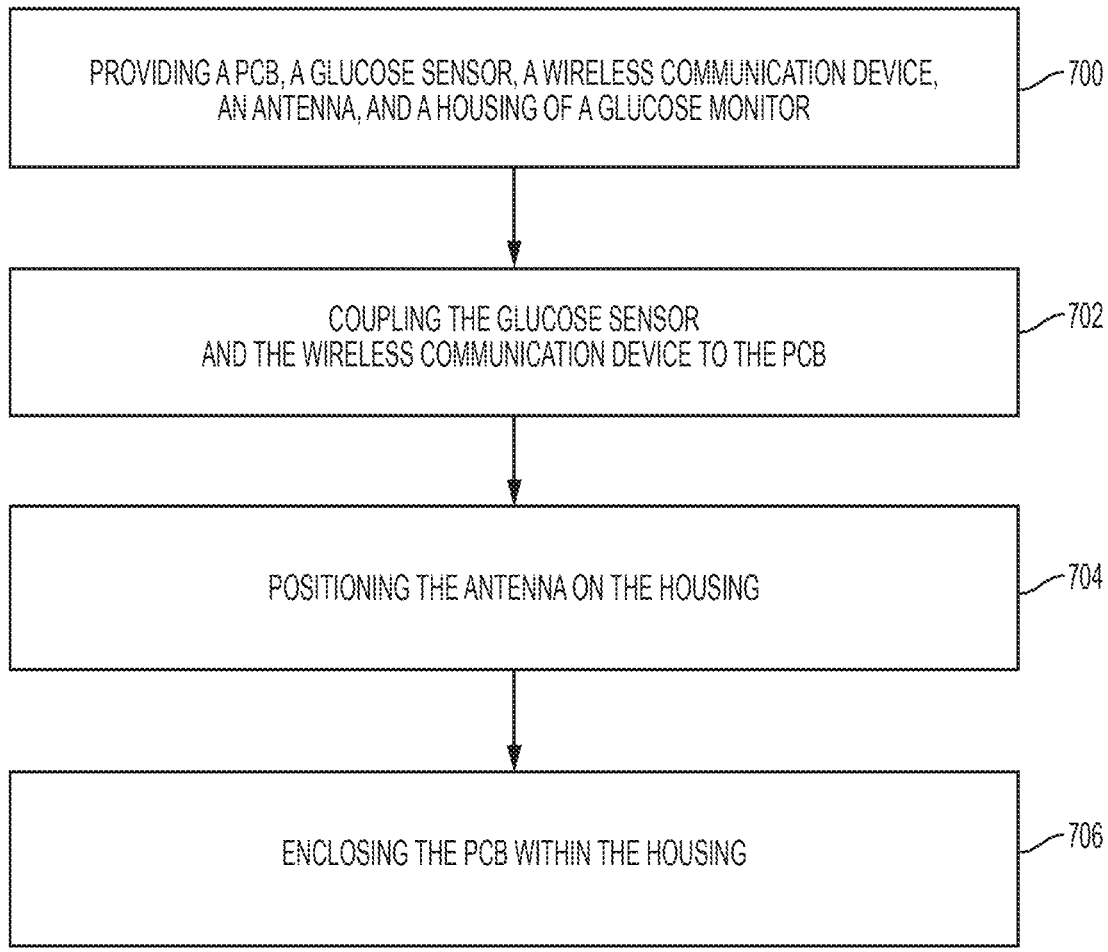
FIG. 7 is a flow chart of a process for assembling a glucose monitor according to aspects of the present disclosure.

FIG. 7 is a flow chart of a process for manufacturing a glucose monitor 100 according to aspects of the present disclosure. The process is described with reference to the figures described herein, though other implementations are possible without departing from the scope of the present disclosure.

In block 700, the PCB 202, the glucose sensor 206, the wireless communication device 212, and the housing 200 are provided. The PCB may be a single-layer PCB or a multi-layer PCB and include conductive tracks to incorporate the electrical components of the glucose monitor 100. The glucose sensor 206 may be an invasive or non-invasive glucose sensor for measuring biological parameters such as glucose levels in the blood. The housing 200 may be a rigid or flexible housing shaped and sized to encapsulate the PCB 202. In some aspects, the housing may include multiple housing sections that together form the housing 200.

In block 702, the glucose sensor 206 and the wireless communication device are coupled to the PCB 202. The wireless communication device 212 is coupled to the PCB 202. The glucose sensor 206 is communicatively coupled to the PCB 202 via a wire, transmission line, electrode circuit, or other conductive material extending from the sensor 206 to the processor 208 on the PCB 202.

In block 704, the antenna 204 is positioned on the housing 200 of the glucose monitor 100. In some aspects, the antenna 204 may be positioned on an external surface of the housing 200. In other aspects, the antenna 204 may be positioned on an internal surface of the housing 200. In some aspects, the housing 200 and the antenna 204 may be distributed into multiple sections and each antenna section may be positioned on a corresponding section of the housing 200. The antenna 204 may be coupled to the PCB 202 by a lead or transmission line extending from the PCB 202 to the antenna 204. In some aspects, the antenna 204 may be coupled to the PCB 202 through the wireless communication device 212 positioned on the PCB 202. For example, a lead may extend from the wireless communication device 212 to the antenna 204 to communicatively couple the antenna to the PCB 202.

In some aspects, a wireless coupling area of the antenna 204 may be defined by an outer trace of the portion of the housing 200 on which the antenna 204 placed. Because the antenna 204 may cover a larger area than the PCB 202, placing the antenna 204 on the housing 200 rather than the PCB 202 may allow the coupling area of the antenna 204 on the housing 200 to be larger than would be allowed by the area of the PCB 202.

In block 706, the PCB 202 is enclosed with the housing 200. In some aspects, the sections of the housing 200 may be combined around the PCB 202 to enclose the PCB 202 within the housing 200. In other aspects, the housing 200 may include a hole through which the PCB 202 is placed and the hole may be sealed temporarily or permanently to enclose the PCB 202 within the housing 200.

Figure 8:
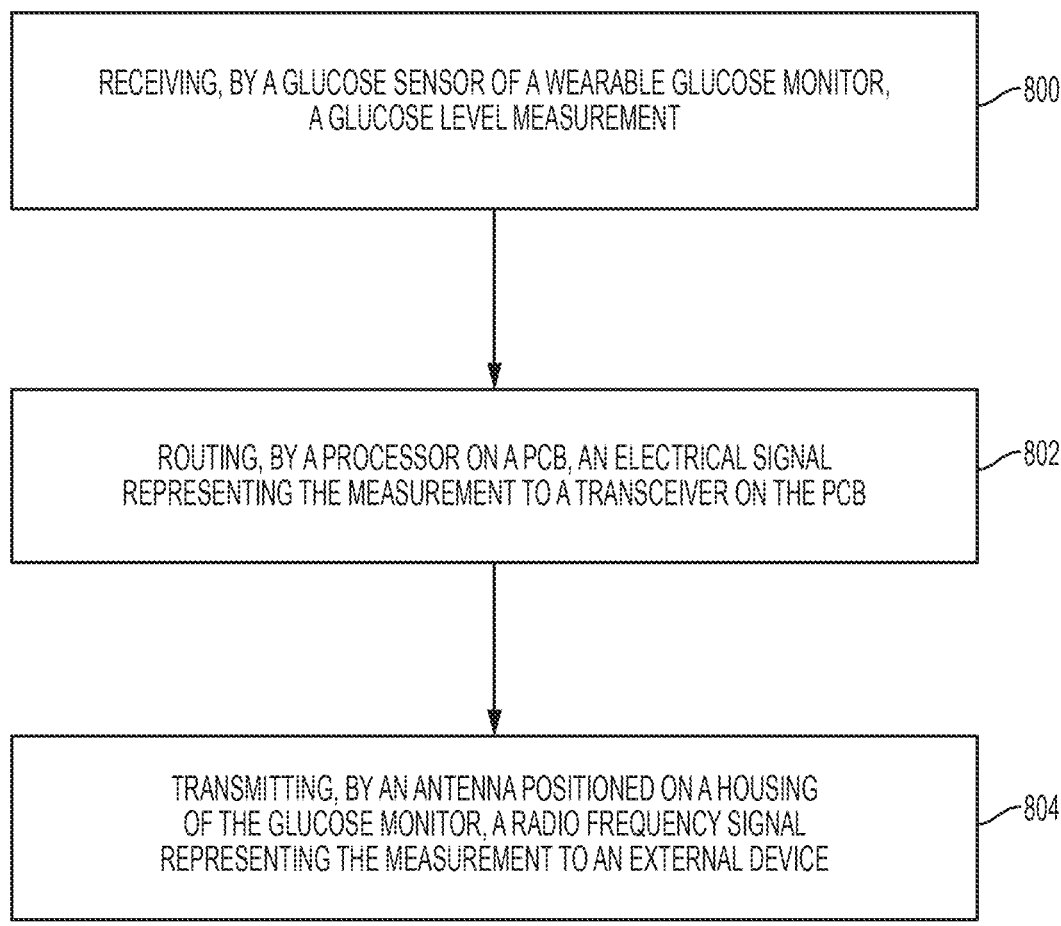
FIG. 8 is a flow chart of a process for wirelessly transmitting a glucose measurement using a glucose monitor according to aspects of the present disclosure.

FIG. 8 is a flow chart of a process for wirelessly transmitting a glucose measurement using a glucose monitor according to aspects of the present disclosure. The process is described with reference to the figures described herein, though other implementations are possible without departing from the scope of the present disclosure.

In block 800, the glucose monitor 100 receives a glucose level measurement from the glucose sensor 206. In some aspects, the glucose sensor 206 may be an invasive sensor including a wire or other insertion means for inserting the glucose sensor 206 into the skin 102 to retrieve a sample of biological fluid from the patient to determine the glucose level measurement of the patient. The glucose sensor 206 may be communicatively coupled to the processor 208 positioned on the PCB 202 and route an electrical signal to the processor 208 corresponding to the glucose level measurement received by the glucose sensor 206.

In block 802, the processor 208 routes an electrical signal representing the glucose level measurement to the wireless communication device 212 via the conductive tracks of the PCB 202. In some aspects, the processor 208 may receive instructions from the memory chip 210 directing the processor 208 to route measurements received from the glucose sensor 206 directly to the wireless communication device 212. In other aspects, the memory chip 210 may instruct the processor 208 to store the measurement in a database and route a set of measurements to the wireless communication device 212 at predetermined intervals, or in response to a signal from the wireless communication device 212 or another PCB 202 component that the antenna 204 is communicatively coupled to the external device 104 for communicating the measurement levels.

In block 804, the antenna 204 transmits a radio frequency signal representing the glucose level measurement to the external device 104. In some aspects, the wireless communication device may route an electrical signal to the antenna 204 corresponding to the glucose level measurement. The antenna 204 may receive a signal from the wireless communication device 212 and generate a radio frequency signal representing the glucose level measurement. The antenna 204 may transmit the radio frequency signal to external device 104 subsequent to communicatively coupling to the antenna 214 of the external device 104.

In some aspects, the antenna 204 of the glucose monitor 100 and the antenna 214 of the external device 104 may be communicatively coupled when the glucose monitor 100 and the external device 104 are positioned within a close proximity of each other, e.g., within 25 centimeters. In some aspects, the radio frequency signal may be transmitted using near-field communications. In other aspects, the radio frequency signal may be transmitted using RFID communications. In some aspects, t radio frequency signal may be transmitted within a frequency range of less than 100 MHz (e.g., 150 kHz for an RFID communication, 13.56 MHz for a near-field communication).

As discussed above, one or more suitable devices according to this disclosure may include a processor or processors. The processor may be in communication with a computer-readable medium, such as a random access memory (RAM) coupled to the processor. The processor executes computer-executable program instructions stored in memory. Such processors may comprise a microprocessor, a digital signal processor (DSP), an application-specific integrated circuit (ASIC), field programmable gate arrays (FPGAs), and state machines. Such processors may further comprise programmable electronic devices such as PLCs, programmable interrupt controllers (PICs), programmable logic devices (PLDs), programmable read-only memories (PROMs), electronically programmable read-only memories (EPROMs or EEPROMs), or other similar devices.

Such processors may comprise, or may be in communication with, media, for example computer-readable storage media, that may store instructions that, when executed by the processor, can cause the processor to perform the steps described herein as carried out, or assisted, by a processor. Examples of computer-readable media may include, but are not limited to, an electronic, optical, magnetic, or other storage device capable of providing a processor with computer-readable instructions. Other examples of media comprise, but are not limited to memory chips, ROM, RAM, ASICs, configured processors, or any other medium from which a computer processor can read. The processor, and the processing, described may be in one or more structures, and may be dispersed through one or more structures. The processor may comprise code for carrying out one or more of the methods (or parts of methods) described herein.

The foregoing description of the examples, including illustrated examples, of the invention has been presented only for the purpose of illustration and description and is not intended to be exhaustive or to limit the invention to the precise forms disclosed. Numerous modifications, adaptations, and uses thereof will be apparent to those skilled in the art without departing from the scope of this invention. The illustrative examples described above are given to introduce the reader to the general subject matter discussed here and are not intended to limit the scope of the disclosed concepts.

Reference herein to an example or implementation means that a particular feature, structure, operation, or other characteristic described in connection with the example may be included in at least one implementation of the disclosure. The disclosure is not restricted to the particular examples or implementations described as such. The appearance of the phrases "in one example," "in an example," "in one implementation," or "in an implementation," or variations of the same in various places in the specification does not necessarily refer to the same example or implementation. Any particular feature, structure, operation, or other characteristic described in this specification in relation to one example or implementation may be combined with other features, structures, operations, or other characteristics described in respect of any other example or implementation.

Use herein of the word "or" is intended to cover inclusive and exclusive OR conditions. In other words, A or B or C includes any or all of the following alternative combinations as appropriate for a particular usage: A alone; B alone; C alone; A and B only; A and C only; B and C only; and A and B and C.

What is claimed is:

1. A wearable device, comprising:
a device housing having a first housing portion and a second housing portion, the first housing portion coupled to the second housing portion;
a printed circuit board ("PCB") disposed in the device housing and communicatively coupled to a sensor to measure a biomedical parameter of a patient; and
an antenna communicatively coupled to the wearable device, the first housing portion having a first portion of the antenna and the second housing portion having a second portion of the antenna, wherein the first portion of the antenna is electrically coupled to the second portion of the antenna by coupling the first housing portion to the second housing portions.

2. The wearable device of claim 1, wherein the sensor comprises an electrochemical sensor.

3. The wearable device of claim 1, wherein the sensor comprises an analyte sensor.

4. The wearable device of claim 1, further comprising a sensor insertable into skin of a patient, wherein the PCB is communicatively coupled to the sensor.

5. The wearable device of claim 1, wherein the sensor comprises a non-invasive sensor.

6. The wearable device of claim 1, wherein the sensor comprises a glucose sensor.

7. The wearable device of claim 1, wherein the first and second housing portions each define a contiguous metal surface having non-metal regions, the contiguous metal surfaces forming the antenna.

8. A wearable device, comprising:
a device housing having a first housing portion and a second housing portion, the first housing portion coupled to the second housing portion;
a printed circuit board ("PCB") disposed in the device housing and communicatively coupled to a sensor to measure a biomedical parameter of a patient; and
an antenna, the first housing portion having a first portion of the antenna and the second housing portion having a second portion of the antenna, wherein the first portion of the antenna is electrically coupled to the second portion of the antenna by coupling the first housing portion to the second housing portions, wherein the antenna comprises a coil.

9. The wearable device of claim 8, wherein the first portion of the antenna comprises a first portion of the coil and the second portion of the antenna comprises a second portion of the coil.

10. The wearable device of claim 9, wherein the first portion of the coil and the second portion of the coil form a three-dimensional coil.

11. The wearable device of claim 10, wherein the three-dimensional coil encircles the PCB.

12. The wearable device of claim 10, wherein an area enclosed by a perimeter of the first portion of the coil or the second portion of the coil disposed on the device housing is larger than an area of the PCB.

13. The wearable device of claim 8, wherein at least a portion of the coil is positioned on an internal surface of the device housing.

14. The wearable device of claim 8, wherein at least a portion of the coil is positioned on an external surface of the device housing.

15. A wearable device, comprising:
a device housing having a first housing portion and a second housing portion, the first housing portion coupled to the second housing portion;
a printed circuit board ("PCB") disposed in the device housing and communicatively coupled to a sensor to measure a biomedical parameter of a patient; and
a plurality of antennas, the first housing portion having a first portion of a first antenna and the second housing portion having a second portion of the first antenna, wherein the first portion of the first antenna is electrically coupled to the second portion of the first antenna by coupling the first housing portion to the second housing portions.

16. The wearable device of claim 15, wherein the first antenna is tuned for a higher frequency range than the second antenna.

17. The wearable device of claim 15, wherein the second antenna is tuned for a higher frequency range than the first antenna.

18. The wearable device of claim 15, wherein a second antenna is positioned on at least one of the first or second portions of the housing.

19. The wearable device of claim 15, wherein at least one of the first antenna or a second antenna is tuned for Bluetooth or wireless local area network communications.

20. The wearable device of claim 15, wherein at least one of the first antenna or a second antenna comprises a near-field communication antenna or a radio-frequency identification antenna.

* * * * *